United States Patent [19]

Walter et al.

[11] Patent Number: 5,569,883
[45] Date of Patent: Oct. 29, 1996

[54] JOINT FOR PROVIDING A SECURE CONNECTION BETWEEN A WOUND ELEMENT AND A MATING PART IN A BODY IMPLANTABLE LEAD ASSEMBLY AND METHOD FOR MAKING SUCH JOINT

[75] Inventors: Jeryle L. Walter, Newhall; Robert J. Hodge, Jr., Valencia; Stephen M. Jones, Canyon Country, all of Calif.

[73] Assignee: Pacesetter, Inc., Sylmar, Calif.

[21] Appl. No.: 299,710

[22] Filed: Aug. 31, 1994

[51] Int. Cl.⁶ ........................................ H01R 4/02
[52] U.S. Cl. .................. 174/84 R; 174/94 R; 607/122; 607/125
[58] Field of Search ............... 174/84 R, 94 R; 439/790, 874; 607/119, 122, 123, 125, 126, 127, 128

[56] References Cited

U.S. PATENT DOCUMENTS

| | | | |
|---|---|---|---|
| 2,093,810 | 9/1937 | Karmazin | 113/112 X |
| 4,033,355 | 7/1977 | Amundson | 128/404 X |
| 4,352,714 | 10/1982 | Patterson et al. | 156/626 X |
| 4,463,765 | 8/1984 | Gold | 128/785 X |
| 5,259,395 | 11/1993 | Li | 607/131 X |
| 5,466,252 | 11/1995 | Soukup et al. | 607/116 X |

*Primary Examiner*—Kristine L. Kincaid
*Assistant Examiner*—Chau N. Nguyen

[57] ABSTRACT

A joint and method of making a joint for providing a secure mechanical and electrical connection between a longitudinally extending coiled or wound element and a terminal on a mating component in a body implantable lead assembly. The wound element has an end portion threadedly received by a post on the terminal. A ring is disposed about the end portion of the wound element. The ring, the end portion of the wound element and the post are joined at at least one location along the circumference of the ring, preferably by thermally fusing these parts using a pulsed laser. The ring has a thin wall and is preferably made of the same biocompatible metallic alloy as the wound element.

13 Claims, 2 Drawing Sheets

JOINT FOR PROVIDING A SECURE CONNECTION BETWEEN A WOUND ELEMENT AND A MATING PART IN A BODY IMPLANTABLE LEAD ASSEMBLY AND METHOD FOR MAKING SUCH JOINT

FIELD OF THE INVENTION

The present invention relates generally to lead assemblies for connecting implantable medical devices with selected body tissue to be stimulated by such devices, and more particularly to techniques for providing a secure electrical and mechanical connection between wound elements, such as coil conductors, and mating parts such as electrodes, sensors and the like, employed within such lead assemblies.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing or for sensing electrical signals produced by the heart or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled or wound conductor surrounded by an insulating tube or sheath couples the connector pin at the proximal end with the electrode at the distal end.

When terminating a wound conductor to an associated electrical element such as a proximal end connector pin, a heart tissue stimulating electrode at the distal end of the lead, a blood oxygen sensor, or other such elements within the lead assembly, there is often no way to statistically ascertain the structural integrity of the termination. These joints must have a high degree of reliability for the implantable product to be acceptable for long term implants such as endocardial type pacing leads. In the past, the only way to verify the joint was to immobilize the mating part and pull on the wound conductor and this technique has been used as the chief test method. The major problem with this approach is that as the winding is pulled unequal tension is applied to the individual strains of the wound conductor. As increased tension is applied to the coil, often one strain breaks sooner than the others yielding erratic test results. The present invention provides an approach that overcomes this test method problem while at the same time providing a very reliable and secure connection between a wound element and a mating component.

Another problem associated with connections between wound elements and mating components in present day lead assemblies arises from the use of different alloys for the wound elements and mating components. Since dissimilar alloys have different melt temperatures such connections are difficult to weld. Moreover, as lead sizes decrease, problems of manufacturability arise. This is particularly true where crimping is employed to secure the wound component to a mating element. See, for example, U.S. Pat. No. 4,953,564 which discloses a cardiac pacing lead having an extendable fixation helix electrode that is mechanically and electrically connected to a rotatable conductor coil by squeezing the helix and coil together between a crimping sleeve and a crimping core. As the sizes of body implantable leads and their constituent parts become smaller, crimping becomes more difficult because the crimping tools cannot be made sufficiently small. Moreover, the same number of lead windings are not always subjected to the crimping action so that failure stress differs from lead to lead.

SUMMARY OF THE INVENTION

In accordance with one specific, exemplary embodiment of the present invention, there is provided a joint for securely connecting a longitudinally extending wound element, such as a coil conductor, with a mating component, such as a terminal on a blood oxygen sensor, housed within the insulative sheath of a body implantable lead assembly. The wound element has a lumen or interior passage and an end portion within which a terminal post of the mating component is received. The joint further includes a ring disposed about the end portion of the wound element; the ring, the end portion of the wound element and the post are joined at at least one location along the circumference of the ring. Preferably, the ring, the end portion of the wound element and the post are joined by thermal fusion using a laser weld. To facilitate such welding, the ring, the wound element and the post are preferably made of the same biocompatible, metallic alloy such as stainless steel.

In accordance with another aspect of the invention, the outer surface of the post is configured to threadedly receive the end portion of the wound element. More specifically, the outer surface of the post has a generally cylindrical configuration with a helical groove formed therein, the end portion of the wound element being received by the helical groove. To further enhance the mechanical and electrical integrity of the joint, the post may have a diameter larger than the diameter of the interior passage of the wound element.

Pursuant to yet another aspect of the present invention, there is provided a method for joining a longitudinally extending wound element, such as a coil conductor, with a terminal on a mating component, such as a blood oxygen sensor, forming parts of a body implantable lead assembly. The wound element has a lumen or longitudinally extending interior passage and an end portion adapted to be received by a post on the terminal of the mating element, the receiving portion of the mating element being configured to receive the end portion of the wound element. The method comprises the steps of placing the end portion of the wound element about the post of the mating element; placing a ring about the end portion of the wound element; and joining the ring, the end portion of the wound element and the post at at least one location along the circumference of the ring. Preferably, the joining step is performed by thermally fusing the parts by laser welding at at least one weld site along the circumference of the ring. The result is a mechanically and electrically secure joint the structural integrity of which may be reliably determined.

BRIEF DESCRIPTION OF THE DRAWINGS

Further objects, features and advantages of the invention will become apparent from the detailed description of the preferred embodiment, below, when read in conjunction with the accompanying drawings in which:

FIGS. 3A, 3B and 3C show the sequence of steps of forming the connection depicted in FIG. 2, and wherein FIG. 3A is a side view of the machined component prior to being connected to the wound conductor, FIG. 3B is a side view of the machined component with the wound conductor threaded on the component and FIG. 3C is a side view of the final configuration of the connection between the wound conductor and mating machined component.

DESCRIPTION OF THE PREFERRED EMBODIMENT

The following description presents a preferred embodiment of the invention representing the best mode contemplated for practicing the invention. This description is not to be taken in a limiting sense but is made merely for the purpose of describing the general principles of the invention whose scope is defined by the appended claims. Moreover, the environment in which the invention is shown herein, that is, a bipolar pacing and sensing lead, is illustrative only; it will be understood by those skilled in the art that the invention may be used to provide electrically and mechanically secure and reliable connections between wound elements and mating components in a wide variety of body implantable leads including but not limited to unipolar leads, multipolar leads (incorporating a shock electrode) and leads with extendable helix fixation electrodes.

Figure 1:
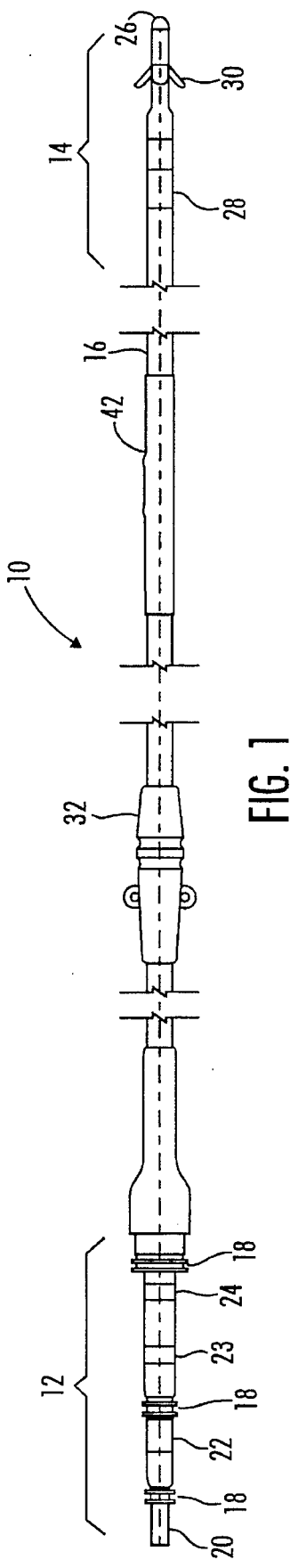
FIG. 1 is a side view of a bipolar, body implantable, intravascular pacing and sensing lead incorporating the present invention.

Referring now to FIG. 1, there is shown a bipolar pacing and sensing lead assembly 10 having a proximal end 12, a distal end 14 and a tubular, insulating sheath or housing 16 made of an insulating biocompatible, biostable material such as polyurethane or silicone rubber, connecting the ends 12 and 14. The proximal end 12 is adapted to be plugged into the socket or receptacle of a cardiac pacemaker (not shown) and for this purpose the elastomeric housing 16 includes longitudinally spaced sets of annular ribs 18 for sealing the pacemaker receptacle against the entry of bodily fluids.

The proximal end 12 of the lead 10 includes a hollow electrical connector pin 20 and three electrically conductive rings 22, 23, and 24 longitudinally spaced apart along the proximal end portion 12. As is well known, the pin 20 and rings 22–24 engage corresponding terminals in the receptacle of the cardiac pacemaker. The distal end 14 of the lead 10 includes a tip electrode 26 and a ring-shaped sensing electrode 28. Projecting from the tubular housing 16 intermediate the electrodes 26 and 28 are four equiangularly spaced tines 30 which engage the heart tissue and urge the tip electrode 26 into contact with the endocardium. Slidably mounted on the lead housing 16 is a fixation or suture sleeve 32 which serves to anchor the lead 10 at the site of venous insertion.

Figure 2:
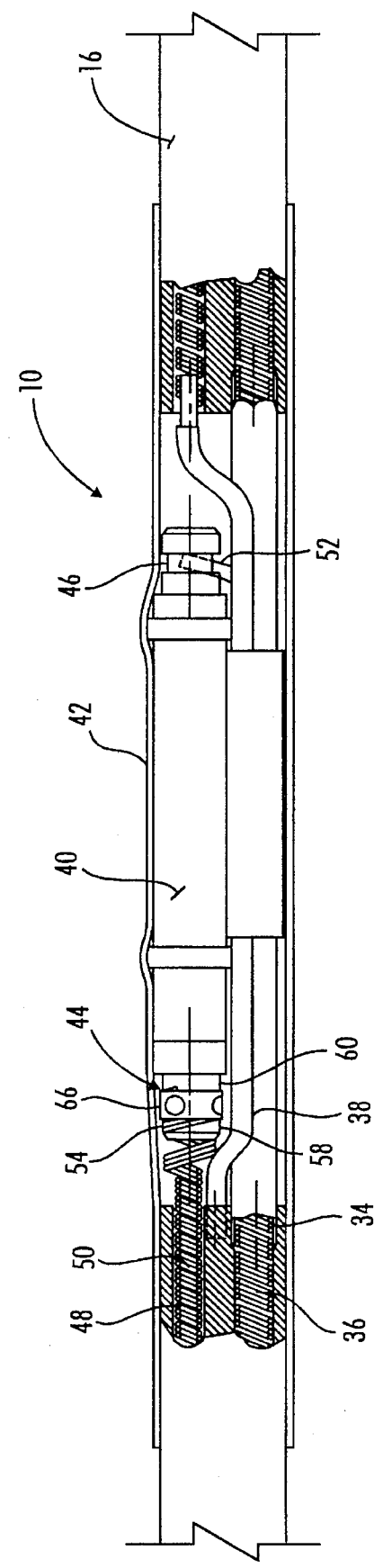
FIG. 2 is a side view, partly in section of a portion of the lead of FIG. 1 showing certain details thereof including a connection between a wound conductor of the lead and a mating machined component in accordance with a preferred embodiment of the invention.

With reference now also to FIG. 2, the hollow connector pin 20 at the proximal end 12 is electrically coupled to the tip electrode 26 by means of a coil conductor 34 enclosed within the tubular housing 16. In accordance with well-known implantation procedures, a stylet (not shown) is passed through the hollow connector pin 20 and the central cavity or lumen 36 of the associated coil conductor 34 to enable the physician to orient the distal end 14 of the lead and to position the tip electrode 26 under fluoroscopy to a desired location in the heart.

The contact ring 22 at the proximal end 12 is electrically coupled to the sensing electrode 28 by a second conductor 38 within the housing 16.

The specific lead assembly 10 shown here by way of example includes a blood oxygen sensor 40 within an insulative sleeve 42 forming part of the housing 16. The sensor 40 is positioned at a location intermediate the proximal and distal ends 12 and 14. The details of the sensor 40 are not illustrated as the construction and operation thereof are well known in the art. Projecting in a longitudinal or axial direction from the proximal and distal ends of the sensor 40 are electrical terminals 44 and 46, respectively. The terminal 44 is electrically coupled to the contact ring 23 by means of a coil or wound conductor 48 having an interior passage 50. The terminal 46 is electrically coupled to the contact ring 24 by means of the series combination of a solid conductor 52 and a coil conductor, the latter being obscured in the view of FIG. 2.

Figure 3A:
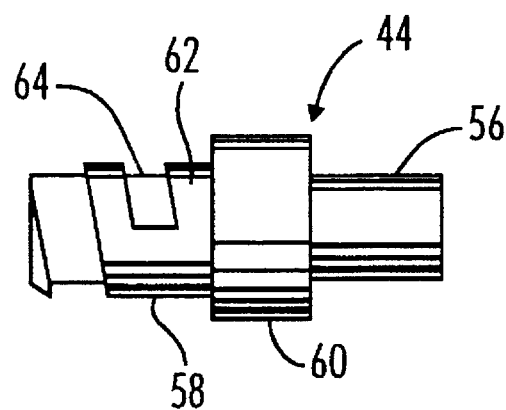
Figure 3B:
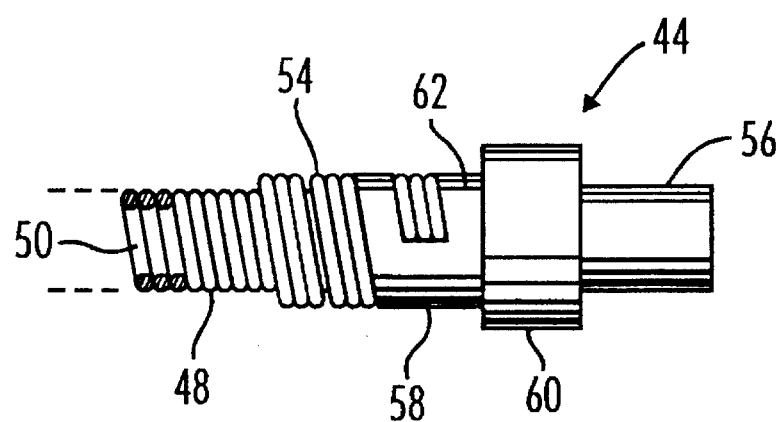
Figure 3C:
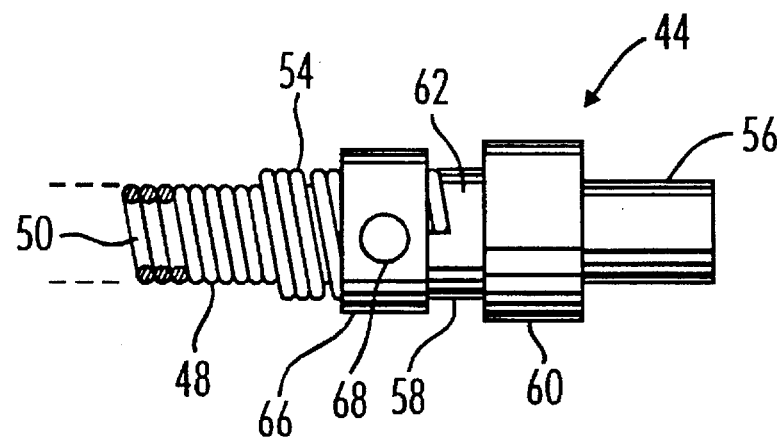

FIGS. 3A–3C show the details of the connection between a distal end portion 54 of the wound conductor 48 and the sensor terminal 44. The terminal 44 is in the form of a generally cylindrical machined component of stainless steel or other biocompatible alloy which is preferably the same alloy as that used to fabricate the wound conductor 48. The terminal 44 includes a pin 56 adapted to be received by the sensor 40; a post 58 for receiving the distal end portion 54 of the wound conductor 48; and an annular flange 60 intermediate the pin 56 and post 58 which flange engages the proximal end of the sensor 40 when the pin 56 of the terminal 44 is in place within the sensor. The post 58 has an outer, generally cylindrical surface 62 having a helical groove 64 machined therein. Preferably, as best seen in FIGS. 3A–3C, the diameter of the post 58 is larger than the diameter of the interior passage 50 of the wound conductor 48. The distal end portion 54 of the wound conductor 48 is threaded onto the helically grooved post 58, as best seen in FIG. 3B. A weld ring 66 is next slipped over the distal end portion 54 of the wound conductor 48 and over the post 58 and all three components 48, 58 and 66 are thermally fused at one or more weld sites 68 using a pulsed laser. The weld ring 66 is preferably made of the same alloy as the wound conductor 48 and terminal 44. Since the melt temperatures will therefore be the same, welding is greatly facilitated. In accordance with one practical example of the invention, the ring 66 can be the thickness of metal foil, for example, about 0.003 inch thick, the ring according to this example further having an inside diameter of about 0.046 inch and a length of about 0.025 inch. If there is sufficient space to accommodate a crimping tool, the ring may be slightly crimped before welding. For a more secure mechanical joint, the inside surface of the ring 66 may be provided with a conical configuration for a force fit over the wound conductor end portion 54.

The joint for connecting a wound element and a mating component in a body implantable lead pursuant to the present invention has been described in the context of the connection between a wound conductor and the terminal of an oxygen sensor. As already explained, it will be evident that the joint and the method for making the joint disclosed herein are equally advantageous for providing secure, reliable mechanical and electrical connections in other body implantable lead contexts. Accordingly, while the invention has been described in connection with a preferred embodiment, it will be understood that it is not intended to limit the invention thereto, but that it is intended to cover all modifications and alternative constructions falling within the spirit and scope of the invention as expressed in the appended claims.

What is claimed is:

1. A method for joining a longitudinally extending wound element and a mating component of a body implantable lead assembly, the wound element having a longitudinally extending interior passage and an end portion adapted to be received by a portion of the mating component, the receiving portion of the mating component being configured to receive the end portion of the wound element, the method comprising the steps of:

placing the end portion of the wound element about the receiving portion of the mating component;

placing a ring about the end portion of the wound element, the ring having a circumference; and joining the ring, the end portion of the wound element and the receiving portion of the mating component at at least one location along the circumference of the ring.

2. The method, as defined in claim 1, in which the ring comprises a weld ring and wherein the joining step is performed by thermally fusing the weld ring, the end portion of the wound element and the receiving portion of the mating component.

3. The method, as defined in claim 2, in which the weld ring, the wound element and the mating component are fabricated of the same alloy.

4. The method, as defined in claim 2, which includes the step of crimping the weld ring before the thermal fusion step.

5. The method, as defined in claim 1, in which:

the receiving portion of the mating component is configured to threadedly receive the end portion of the wound element.

6. The method, as defined in claim 5, in which the receiving portion of the mating component has an outer surface provided with a generally helical groove for receiving the end portion of the wound element.

7. The method, as defined in claim 1, in which the receiving portion of the mating component has a diameter that is larger than the diameter of the interior passage of the wound element.

8. A joint connecting a longitudinally extending wound element and a mating component of a body implantable lead assembly, the wound element having an interior passage and an end portion, the mating component having a post for receiving the end portion of the wound element, the post having an outer surface, the end portion of the wound element being disposed about the post and being in engagement with the outer surface thereof, the joint further comprising a ring disposed about the end portion of the wound element; the ring, the end portion of the wound element and the post being joined at at least one location along the circumference of the ring.

9. The joint, as defined in claim 8, in which the ring, the end portion of the wound element and the post are joined by thermal fusion.

10. The joint, as defined in claim 9, in which the ring, the wound element and the post are made of substantially the same biocompatible, metallic alloy.

11. The joint, as defined in claim 8, in which the outer surface of the post is configured to threadedly receive the end portion of the wound element.

12. The joint, as defined in claim 11, in which the outer surface of the post has a generally cylindrical configuration with a helical groove formed therein, the end portion of the wound element being received by the helical groove.

13. The joint, as defined in claim 12, in which the post has a diameter larger than the diameter of the interior passage of the wound element.

* * * * *